United States Patent
Lingappa et al.

(10) Patent No.: US 9,382,221 B2
(45) Date of Patent: Jul. 5, 2016

(54) COMPOUNDS, COMPOSITIONS, AND METHODS FOR TREATING ALZHEIMER'S DISEASE

(71) Applicant: Prosetta Antiviral Inc., San Francisco, CA (US)

(72) Inventors: Vishwanath Lingappa, San Francisco, CA (US); Clarence R. Hurt, Los Altos, CA (US)

(73) Assignee: Prosetta Antiviral Inc., San Francisco, CA (US)

( * ) Notice: Subject to any disclaimer, the term of this patent is extended or adjusted under 35 U.S.C. 154(b) by 0 days.

(21) Appl. No.: 14/323,346

(22) Filed: Jul. 3, 2014

(65) Prior Publication Data

US 2014/0315897 A1 Oct. 23, 2014

Related U.S. Application Data

(62) Division of application No. 13/316,423, filed on Dec. 9, 2011, now Pat. No. 8,796,448.

(60) Provisional application No. 61/477,203, filed on Apr. 20, 2011, provisional application No. 61/468,614, filed on Mar. 29, 2011, provisional application No. 61/453,571, filed on Mar. 17, 2011, provisional application No. 61/421,225, filed on Dec. 9, 2010.

(51) Int. Cl.
*C07D 279/20* (2006.01)

(52) U.S. Cl.
CPC ................................... *C07D 279/20* (2013.01)

(58) Field of Classification Search
CPC .................................................... C07D 279/20
USPC ................................. 514/225.8, 224.8, 225.2
See application file for complete search history.

(56) References Cited

U.S. PATENT DOCUMENTS 7,737,138 B2 * 6/2010 Wischik et al. ............ 514/224.8
2003/0181389 A1 * 9/2003 Wulfert et al. ................... 514/18

FOREIGN PATENT DOCUMENTS

| GB | 2083488 A | | 3/1982 |
|---|---|---|---|
| WO | WO 9630766 A1 | * | 10/1996 |
| WO | WO2002003972 A | * | 1/2002 |

* cited by examiner

*Primary Examiner* — Kahsay Habte
(74) *Attorney, Agent, or Firm* — Morgan, Lewis & Bockius LLP

(57) ABSTRACT

Novel methods and compounds for treating Alzheimer's Disease are provided. In one aspect, the invention provides methods for treating Alzheimer's Disease by administering certain phenothiazine derivatives. In one embodiment, the methods include administering an effective amount of a 3-oxo-7-dialkyl-amino-phenothiazine derivative, or 3-oxo-7-dialkyl-amino-phenothiazine. In another embodiment, the invention provides methods for treating Alzheimer's Disease by administering an effective amount of a 3,7-diazetidin-1-yl-phenothiazine or a derivative thereof. In another aspect, the invention provides novel azetidinyl phenothiazine compounds.

19 Claims, No Drawings

COMPOUNDS, COMPOSITIONS, AND METHODS FOR TREATING ALZHEIMER'S DISEASE

CROSS-REFERENCES TO RELATED APPLICATIONS

This application is a divisional of U.S. application Ser. No. 13/316,423, filed Dec. 9, 2011, now U.S. Pat. No. 8,796,448, and is a continuation-in-part of U.S. patent application Ser. No. 13/423,141, filed Mar. 16, 2012, now U.S. Pat. No. 8,759,336, and is a continuation-in-part of Ser. No. 13/433,378, filed Mar. 29, 2012, now U.S. Pat. No. 8,809,317, and is a continuation-in-part of Ser. No. 13/451,608, filed Apr. 20, 2012, now U.S. Pat. No. 8,828,986, and claims the benefit of U.S. Provisional Application No. 61/421,225, filed Dec. 9, 2010, 61/453,571, filed Mar. 17, 2011, 61/468,614, filed Mar. 29, 2011, 61/477,203, filed Apr. 20, 2011, the entire disclosure of U.S. Patent Application Ser. No. 61/421,225, filed Dec. 9, 2010 is incorporated by reference in its entirety for all purposes.

1. BACKGROUND OF THE INVENTION

1.1 Field of the Invention

The present invention provides compounds, compositions, and methods for treating Alzheimer's disease. The present invention has applications in the areas of medicine, medicinal chemistry, and neurobiology.

1.2 The Related Art

Alzheimer's Disease ("AD"), also known as Alzheimer disease, senile dementia of the Alzheimer type ("SDAT"), primary degenerative dementia of the Alzheimer's type ("PDDAT"), or simply as "Alzheimer's", named after Alois Alzheimer, who first described the ailment in 1906, is the most common form of dementia, usually striking those over 65 years. "Early-onset Alzheimer's", which affects far fewer individuals, can strike much earlier. (Hereinafter, all forms of the disease will be referred to as "Alzheimer's" or "AD" unless specifically noted otherwise.) Current estimates place the number of Alzheimer's sufferers at nearly 27 million; the disease is expected to affect about one in every 85 persons by 2050. Alzheimer's is incurable, degenerative, and terminal.

Although the etiology of the disease is not known, and the course of the disease varies among individuals, there are common early symptoms, such as the inability to acquire new memories as manifested by failing to recall recent observations. Often, these early symptoms are mistakenly identified as "age-related" concerns or stress reactions. The diagnosis of AD is typically made using behavioral assessments, cognitive tests, and brain scans. However, the disease develops over a variable period before becoming fully apparent and often goes undiagnosed for years.

Symptoms of advancing AD include confusion, irritability and aggression, mood swings, language breakdown, long-term memory loss, and the general withdrawal of the sufferer as their senses decline. The sufferer's bodily functions slowly deteriorate until they are lost, leading to death. Individual prognosis is difficult to assess, as the duration of the disease varies. The mean life expectancy following diagnosis is approximately seven years; fewer than three percent of individuals live more than fourteen years after diagnosis.

Current theories describing the mechanism of Alzheimer's posit that the disease is related to the development of various plaques and tangles in the brain. Analysis of these plaques reveals an abundance of the so-called Aβ peptide, an approximately 40-residue protein fragment partially overlapping a sequence in the transmembrane and cytosolic domains of a 100 kDa gene product termed the amyloid precursor protein ("APP"). The Aβ peptide has been shown to occur in both monomeric and oligomeric forms, with Aβ oligomers having been demonstrated to be toxic to neurites in cell culture. Formation of such oligomers is accentuated by APP mutations that are associated with familial AD. Thus, in theory a small molecule which blocked Aβ oligomer formation in cell culture would be a promising candidate for an AD therapeutic or prophylactic. But many questions remain to be answered before a comprehensive theory of the AD disease process is available.

Current treatments can offer only minor symptomatic relief; there are no treatments capable of slowing or halting disease progression. But the lack of effective palliative treatments or outright cure is not for any lack of trying: As of 2008, more than 500 clinical trials have been conducted on possible treatments for AD, but none has shown significant results. Both the professional and popular literature and media have touted various life-styles to prevent Alzheimer's disease, but there is scant evidence of any causal link between these recommendations and disease prevention or improvement.

Because AD cannot be cured and is degenerative, the careful management of patients suffering from this disease is essential—and usually falls heavily on family members in view of the astronomical costs of professional care. The pressures resulting for taking care of Alzheimer's patients impact nearly every aspect of the caregiver's life, including their social, psychological, physical, and economic well being. Not surprisingly, Alzheimer's Disease is one of the most costly diseases among all industrial societies.

New treatments are thus needed desperately to combat this horrific disease. The present invention meets this and other needs.

2. SUMMARY OF EMBODIMENTS OF THE INVENTION

In a first aspect, the present invention provides methods for treating Alzheimer's Disease. In one embodiment, the invention provides a method for treating Alzheimer's Disease, comprising administering to a mammal suffering from such disease a therapeutically effective amount of a compound having the structure:

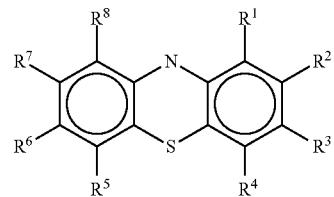

and its pharmaceutically acceptable salts, hydrates, and coordination compounds. $R^1$, $R^2$, $R^4$, $R^5$, $R^7$, and $R^8$ are selected independently from the group consisting of: hydrogen, halo, cyano, nitro, nitrilo, hydroxy, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, hetcroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl) alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsulfonyl, cycloalkylsulfonyl, aralkycarbonylthioooxy, carbonylythio, heteroaralkylcarbonylthio, (cycloalkyloxy)carbonylthio, (cycloheteroalkyl) alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl) and (cycloheteroalkyl)iminoalkyl. $R^3$ and $R^6$ are selected independently from the group consisting of: optionally substituted four-, five-, six-, or seven-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl; and oxo, thiocarbonyl, imino, and optionally substituted dialkylimino, diarylimino, di-heteroarylimino, alkylarylimino, alkylheteroarylimino, arylheteroarylimino, amino, alkylamino, dialkylamino, alkyloxyalkylamino, di(alkyloxyalkyl)amino, alkylthioalkylamino, di(alkylthioalkyl)amino, alkylaminoalkylamino, di-(alkylamino alkyl) amino, aryloxyalkylamino, di-(aryloxyalkyl)amino, arylthioalkylamino, di(arylthioalkyl)amino, arylaminoalkylamino, di-(arylaminoalkyl)amino, heteroaryloxyalkylamino, di(heteroaryloxyalkyl)amino, heteroarylthioalkylamino, di(heteroarylthioalkyl)amino, heteroarylaminoalkylamino, and di(heteroarylaminoalkyl)amino. However, at least one of $R^3$ and $R^6$ is optionally substituted dialkyalamino or optionally substituted five-, six-, or seven-membered cycloheteroalkyl, said cycloheteroalkyl including a first ring nitrogen heteroatom bonded at the position indicated by $R^3$ or $R^6$, respectively.

In a more specific embodiment, each of $R^3$ and $R^6$ is optionally substituted dialkylamino. Among these compounds, more specific embodiments include those for which each of $R^1$, $R^2$, $R^4$, $R^5$, $R^7$, and $R^8$ is hydrogen. Still more specific embodiments include those for which each of $R^1$, $R^2$, $R^4$, $R^5$, $R^7$, and $R^8$ is hydrogen, and each of $R^3$ and $R^6$ is dialkylamino; and, yet more specifically, each of $R^3$ and $R^6$ is diethylamino or dimethylamino; and still more specifically each of $R^3$ and $R^6$ is dimethylamino.

In other more specific embodiments of the method of the invention, each of $R^3$ and $R^6$ in the compound illustrated above is optionally substituted dialkylamino and each of $R^2$, $R^4$, $R^5$, and $R^7$ is hydrogen. In more specific embodiments, each of $R^2$, $R^4$, $R^5$, and $R^7$ is hydrogen and each of $R^3$ and $R^6$ is dialkylamino; more specifically each of $R^3$ and $R^6$ is diethylamino or dimethylamino; and still more specifically each of $R^3$ and $R^6$ is dimethylamino. Among the embodiments in which each of $R^3$ and $R^6$ is dimethylamino and each of $R^2$, $R^4$, $R^5$, and $R^7$ is hydrogen, more specific embodiments are those for which at least one of $R^1$ and $R^8$ is optionally substituted lower-alkyl; more specifically at least one of $R^1$ and $R^8$ is optionally substituted ethyl or methyl; still more specifically at least one of $R^1$ and $R^8$ is methyl or trifluoromethyl. Yet more specific embodiments are those in which each of $R^3$ and $R^6$ is dimethylamino and each of $R^2$, $R^4$, $R^5$, and $R^7$ is hydrogen and each of $R^1$ and $R^8$ is methyl. Other more specific embodiments are those in which each of $R^3$ and $R^6$ is dimethylamino and each of $R^2$, $R^4$, $R^5$, and $R^7$ is hydrogen, and one of $R^1$ and $R^8$ is trifluoromethyl and the other of $R^1$ and $R^8$ is hydrogen.

In other embodiments of the method of the invention, $R^3$ of the compound illustrated above is oxo. In more specific embodiments of these compounds, each of $R^1$, $R^2$, $R^4$, $R^5$, $R^7$, and $R^8$ is hydrogen. Still more specific embodiments are those for which $R^3$ of the compound illustrated above is oxo, each of $R^1$, $R^2$, $R^4$, $R^5$, $R^7$, and $R^8$ is hydrogen, and $R^6$ is optionally substituted dialkylamino, yet more specifically, optionally substituted diethylamino or dimethylamino, and, still yet more specifically, dimethylamino.

In still other embodiments, referring to the structure above, each of $R^3$ and $R^6$ is optionally substituted four-, five-, six-, or seven-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl. Of these embodiments, more specific embodiments are those for which each of $R^3$ and $R^6$ is optionally substituted five-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl. Still more specific embodiments include those in which each of $R^3$ and $R^6$ is optionally substituted pyrrolidin-1-yl, and still more specifically, those for which each of $R^3$ and $R^6$ is pyrrolidin-1-yl. Among these last embodiments more specific embodiments, include those in which each of $R^1$, $R^2$, $R^4$, $R^5$, $R^7$, and $R^8$ is hydrogen.

In another aspect, the present invention provides novel compounds having the general structure:

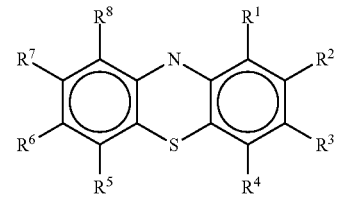

and its pharmaceutically acceptable salts, hydrates, and coordination compounds. $R^1$, $R^2$, $R^4$, $R^5$, $R^7$, and $R^8$ are selected independently from the group consisting of: hydrogen, halo, cyano, nitro, nitrilo, hydroxy, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl) alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsulfonyl, cycloalkylsulfonyl, aralkycarbonylthioooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cyclo alkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl. At least one of $R^3$ and $R^6$ is optionally substituted azetidin-1-yl.

3. DETAILED DESCRIPTION OF SOME EMBODIMENTS OF THE INVENTION

3.1 Definitions

The following terms are used herein as defined below unless specifically stated otherwise:

Optionally substituted refers to the replacement of hydrogen with a univalent or divalent radical. Suitable substitution groups include, for example, hydroxyl, nitro, amino, imino, cyano, halo, thio, thioamido, ainidino, oxo, oxamidino, methoxamidino, imidino, guanidino, sulfonamido, carboxyl, formyl, loweralkyl, haloloweralkyl, loweralkoxy, haloloweralkoxy, loweralkoxyakyl, alkylcarbonyl, arylcarbonyl, aralkylcarbonyl, heteroarylcarbonyl, heteroaralkylcarbonyl, alkylthio, aminoalkyl, cyanoalkyl, and the like as defined herein. The substitution group can itself be substituted. The group substituted onto the substitution group can be, for example, carboxyl, halo, nitro, amino, cyano, hydroxyl, loweralkyl, loweralkoxy, aminocarbonyl, —SR, thioamido, —$SO_3H$, —$SO_2R$ or cycloalkyl, where R is typically hydrogen, hydroxyl or loweralkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

Loweralkyl as used herein refers to branched or straight chain alkyl groups comprising one to ten carbon atoms that independently are unsubstituted or substituted, e.g., with one or more halogen, hydroxyl or other groups. Examples of loweralkyl groups include, but are not limited to, methyl, ethyl, propyl, isopropyl, n-butyl, t-butyl, n-hexyl, neopentyl, trifluoromethyl, pentafluoroethyl, and the like.

Alkylenyl refers to a divalent straight chain or branched chain saturated aliphatic radical having from 1- to 20 carbon atoms. Typical alkylenyl groups employed in compounds of the present invention are loweralkylenyl groups that have from 1 to about 6 carbon atoms in their backbone.

Alkenyl refers herein to straight chain, branched, or cyclic radicals having one or more double bonds and from 2 to 20 carbon atoms.

Alkynyl refers herein to straight chain, branched, or cyclic radicals having one or more triple bonds and from 2 to 20 carbon atoms.

Haloloweralkyl refers to a loweralkyl radical substituted with one or more halogen atoms.

Loweralkoxy as used herein refers to RO— wherein R is loweralkyl. Representative examples of loweralkoxy groups include methoxy, ethoxy, t-butoxy, trifluoromethoxy and the like.

Loweralkylhio as used herein refers to RS— wherein R is loweralkyl.

Alkoxyalkyl refers to the group-$alk_1$-O-$alk_2$, where $alk_1$ is alkylenyl or alkenyl, and $alk_2$ is alkyl or alkenyl.

Loweralkoxyalkyl refers to an alkoxyalkyl as defined above, where $alk_1$ is loweralkylenyl or loweralkenyl, and $alk_2$ is loweralkyl or loweralkenyl.

Aryloxyalkyl refers to the group alkylenyl-O-aryl. The term Aralkoxyalkyl refers to the group alkylenyl-O-alkyl, where aralkyl is a loweraralkyl.

Cycloalkyl refers to a mono- or polycyclic, loweralkyl substituent. Typical cycloalkyl substituents have from 3 to 8 backbone (i.e., ring) atoms in which each backbone atom is optionally substituted carbon. When used in context with cycloalkyl substituents, the term polycyclic refers herein to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

Cycloheteroalkyl refers herein to cycloalkyl substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpryolidinyl, pyrrolidinone-yl, and the like.

(Cycloalkyl)alkyl and (Cycloheteroalkyl)alkyl refer to alkyl chains substituted with cycloalkyl and cycloheteroalkyl groups respectively.

Haloalkoxy refers to an alkoxy radical substituted with one or more halogen atoms. The term haloloweralkoxy refers to a loweralkoxy radical substituted with one or more halogen atoms.

Halo refers herein to a halogen radical, such as fluorine, chlorine, bromine, or iodine.

Aryl refers to monocyclic and polycyclic aromatic groups, or fused ring systems having at least one aromatic ring, having from 3 to 14 backbone carbon atoms. Examples of aryl groups include without limitation phenyl, naphthyl, dihydronaphtyl, tetrahydronaphthyl, and the like.

Aralkyl refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Heteroaryl refers herein to aryl groups having from one to four heteroatoms as ring atoms in an aromatic ring with the remainder of the ring atoms being aromatic or non-aromatic carbon atoms. When used in connection with aryl substituents, the term polycyclic refers herein to fused and non-fused cyclic structures in which at least one cyclic structure is aromatic, such as, for example, benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

Amino refers herein to the group —$NH_2$. The term loweralkylamino refers herein to the group —NRR' where R and R' are each independently selected from hydrogen or loweralkyl. The term arylamino refers herein to the group —NRR' where R is aryl and R' is hydrogen, loweralkyl, aryl, or aralkyl. The term aralkylamino refers herein to the group —NRR' where R is aralkyl and R' is hydrogen, loweralkyl, aryl, or aralkyl. The terms heteroarylamino and heteroaralkylamino are defined by analogy to arylamino and aralkylamino.

Aminocarbonyl refers herein to the group —C(O)—NH$_2$. The terms loweralkylaminocarbonyl, arylaminocarbonyl, aralkylaminocarbonyl, heteroarylaminocarbonyl, and heteroaralkylaminocarbonyl refer to —C(O)NRR' where R and R' independently are hydrogen and optionally substituted loweralkyl, aryl, aralkyl, heteroaryl, and heteroaralkyl respectively by analogy to the corresponding terms above.

Thio refers to —SH. The terms loweralkylthio, arylthio, heteroarylthio, cycloalkylthio, cycloheteroalkylthio, aralkylthio, heteroaralkylthio, (cycloalkyl)alkylthio, and (cycloheteroalkyl)alkylthio refer to —SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfonyl refers herein to the group —SO$_2$—. The terms loweralkylsulfonyl, arylsulfonyl, heteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl refer to —SO$_2$R where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfinyl refers herein to the group —SO—. The terms loweralkylsulfinyl, arylsulfonyl, heteroarylsulfinyl, cycloalkylsulfinyl, cycloheteroalkylsulfinyl, aralkylsulfinyl, heteroaralkylsulfinyl, (cycloalkyl)alkylsulfinyl, and (cycloheteroalkyl)alkylsulfinyl refer to —SOR where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Formyl refers to —C(O)H.

Carboxyl refers to —C(O)OH.

Carbonyl refers to the divalent group —C(O)—. The terms loweralkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, and (cycloheteroalkyl)alkylcarbonyl refer to —C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Thiocarbonyl refers to the group —C(S)—. The terms loweralkylthiocarbonyl, arylthiocarbonyl, hetelvarylthiocarbonyl, cycloalkylthiocarbonyl, cycloheteroalkylthiocarbonyl, aralkylthiocarbonyloxlthiocarbonyl, heteroaralkylthiocarbonyl, (cycloalkyl)alkylthiocarbonyl, and (cycloheteroalkyl)alkylthiocarbonyl refer to —C(S)R, where R is optionally substituted loweralkyl, aryl, heteroaryl, cycloalkyl, cycloheteroalkyl, aralkyl, heteroaralkyl, (cycloalkyl)alkyl and (cycloheteroalkyl)alkyl respectively.

Carbonyloxy refers generally to the group —C(O)—O—. The terms loweralkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy refer to —C(O)OR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Oxycarbonyl refers to the group —O—C(O)—. The terms loweralkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl)alkyloxycarbonyl refer to —O—C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonylamino refers to the group —NH—C(O)—. The terms loweralkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, and (cycloheteroalkyl)alkylcarbonylamino refer to —NH—C(O)R—, where R is optionally substituted loweralkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present invention includes n-substituted carbonylamino (—NR'C(O)R), where R' is optionally substituted loweralkyl, aryl, heteroaryl, aralkyl, or heteroaralkyl and R retains the previous definition.

Carbonylthio refers to the group —C(O)—S—. The terms loweralkylcarbonylthio, arylcarbonylthio, heteroarylcarbonylthio, cycloalkylcarbonylthio, cycloheteroalkylcarbonylthio, aralkylcarbonylthio, heteroaralkylcarbonylthio, (cycloalkyl)alkylcarbonylthio, (cycloheteroalkyl)alkylcarbonylthio refer to —C(O)SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Guanidino or Guanidyl refers to substituents having a skeleton derived from guanidine, H$_2$N—C(=NH)—NH$_2$. Such moieties include those bonded at the nitrogen atom carrying the formal double bond (the 2-position of the guanidine, e.g., diaminomethyleneamino, ((H$_2$N)$_2$—C=NH—) and those bonded at either of the nitrogen atoms carrying a formal single bond (the 1- or 3-positions of the guanidine, e.g., H$_2$N—C(=NH)—NH—). The hydrogen atoms at either nitrogen can be replaced with a suitable substituent, such as loweralkyl, aryl, or loweraralkyl.

Amidino refers to the moieties R—C(=N)—NR'—(the radical being at the N$^1$ nitrogen) and R(NR')C=N—(the radical being at the N$^2$ nitrogen), where R and R' can be hydrogen, loweralkyl, aryl, or loweraralkyl.

Imino refers to the group —C(=NR)—, where R can be hydrogen or optionally substituted loweralkyl, aryl, heteroaryl, or heteroaralkyl respectively. The terms iminoloweralkyl, iminocycloalkyl, iminocycloheteroalkyl, iminoaralkyl, iminoheteroaralkyl, (cycloalkyl)iminoalkyl, (cycloiminoalkyl)alkyl, (cycloiminoheteroalkyl)alkyl, and (cycloheteroalkyl)iminoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an imino group, respectively.

Oximino refers to the group —C(=NOR)—, where R can be hydrogen (hydroximino) or optionally substituted loweralkyl, aryl, heteroaryl, or heteroaralkyl respectively. The terms oximinoloweralkyl, oximinocycloalkyl, oximinocycloheteroalkyl, oximinoaralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an oximino group, respectively.

Methylene as used herein refers to an unsubstituted, monosubstituted, or disubstituted carbon atom having a formal sp$^3$ hybridization (i.e., —CRR'—, where R and R' are hydrogen or independent substituents).

Methine as used herein refers to an unsubstituted or substituted carbon atom having a formal sp$^2$ hybridization (i.e., CR= or =CR—, where R is hydrogen or a substituent).

3.2 Compounds and Methods for Treating Alzheimer's Disease

In a first aspect, the present invention provides a method for treating Alzheimer's Disease. In one embodiment, the method of the invention comprises administering to a mammal suffering from such disease a therapeutically effective amount of a compound having the structure:

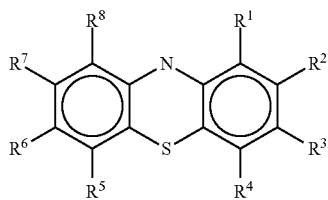

and its pharmaceutically acceptable salts, hydrates, and coordination compounds, wherein:

$R^1$, $R^2$, $R^4$, $R^5$, $R^7$, and $R^8$ are selected independently from the group consisting of: hydrogen, halo, cyano, nitro, nitrilo, hydroxy, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsulfonyl, cycloalkylsulfonyl, aralkycarbonylthioooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl;

$R^3$ and $R^6$ are selected independently from the group consisting of: optionally substituted four-, five-, six-, or seven-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl; and oxo, thiocarbonyl, imino, and optionally substituted dialkylimino, diarylimino, di-heteroarylimino, alkylarylimino, alkylheteroarylimino, arylheteroarylimino, amino, alkylamino, dialkylamino, alkyloxyalkylamino, di-(alkyloxyalkyl)amino, alkylthioalkylamino, di(alkylthioalkyl)amino, alkylaminoalkylamino, di-(alkylaminoalkyl)amino, aryloxyalkylamino, di-(aryloxyalkyl)amino, arylthioalkylamino, di(arylthioalkyl)amino, arylaminoalkylamino, di-(arylaminoalkyl)amino, heteroaryloxyalkylamino, di-(heteroaryloxyalkyl)amino, heteroarylthioalkylamino, di-(heteroarylthioalkyl)amino, heteroarylaminoalkylamino, and di-(heteroarylaminoalkyl)amino; and at least one of $R^3$ and $R^6$ is optionally substituted dialkylamino or optionally substituted five-, six-, or seven-membered cycloheteroalkyl, said cycloheteroalkyl including a first ring nitrogen heteroatom bonded at the position indicated by $R^3$ or $R^6$, respectively.

Those having ordinary skill in the art will appreciate that compounds having the structure of Compound 1 can exist in a variety of formal hybridization structures that may or may not include a formal charge; thus, the structural formula for Compound 1 shown above implicitly includes all equivalent resonance structures including any charges. Similarly, the illustration of any specific resonance structure herein is defined to include all equivalent resonance structures implicitly unless specifically noted otherwise. The identification of such resonance structures and their equivalents is well known to persons having ordinary skill in the art.

In some embodiments, each of $R^3$ and $R^6$ described above is optionally substituted dialkylamino. Among these embodiments, more specific embodiments include those in which each of $R^1$, $R^2$, $R^4$, $R^5$, $R^7$, and $R^8$ is hydrogen. Still more specific embodiments are those in which each of $R^1$, $R^2$, $R^4$, $R^5$, $R^7$, and $R^8$ is hydrogen and each of $R^3$ and $R^6$ is dialkylamino, and still more specifically, each of $R^3$ and $R^6$ is diethylamino or dimethylamino. Yet more specifically, each of $R^1$, $R^2$, $R^4$, $R^5$, $R^7$, and $R^8$ is hydrogen and each of $R^3$ and $R^6$ is dimethylamino, i.e., methylene blue (Compound 2).

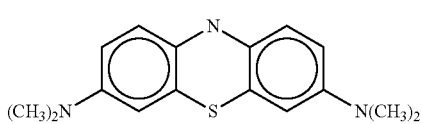

In other embodiments, each of $R^3$ and $R^6$ described above (Compound 1) is optionally substituted dialkylamino and each of $R^2$, $R^4$, $R^5$, and $R^7$ is hydrogen. In more specific embodiments, each of $R^2$, $R^4$, $R^5$, and $R^7$ is hydrogen and each of $R^3$ and $R^6$ is dialkylamino, and in more particular embodiments, each of $R^3$ and $R^6$ is diethylamino or dimethylamino. In still more particular embodiments, each of $R^2$, $R^4$, $R^5$, and $R^7$ is hydrogen and each of $R^3$ and $R^6$ is dimethylamino. Among those embodiments, still more specific embodiments are those in which at least one of $R^1$ and $R^8$ is optionally substituted lower-alkyl, and, in more particular embodiments, at least one of $R^1$ and $R^8$ is optionally substituted ethyl or methyl. Among these embodiments, yet more specific embodiments are those in which at least one of $R^1$ and $R^8$ is methyl or trifluoromethyl. Two particular embodiments from among those just described are those in which each of $R^2$, $R^4$, $R^5$, and $R^7$ is hydrogen and each of $R^3$ and $R^6$ is dimethylamino and each of $R^1$ and $R^8$ is methyl (Compound 3) and those in which each of $R^2$, $R^4$, $R^5$, and $R^7$ is hydrogen and one of $R^1$ and $R^8$ is trifluoromethyl and the other of $R^1$ and $R^8$ is hydrogen (Compound 4).

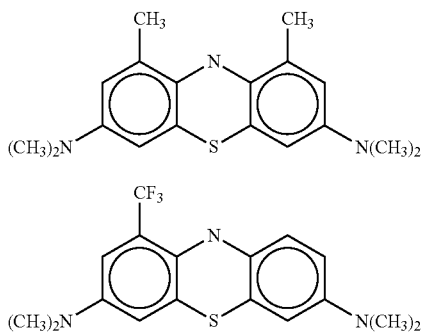

More examples of useful compounds having such structural features can be found in co-pending U.S. patent application Ser. No. 12/062,491, the entire disclosure of which is incorporated herein by reference in its entirety and for all purposes.

Still other useful compounds are those for which each of $bR^3$ and $R^6$ is optionally substituted dialkyloxyalkylamino, dialkyloxyalkylamino, and more particularly di(methyloxyethyl)amino. Among those embodiments, still more specific embodiments are those in which at least one of $R^1$ and $R^8$ is optionally substituted lower-alkyl, and, in more particular embodiments, at least one of $R^1$ and $R^8$ is optionally substituted ethyl or methyl. Further examples of such compounds can be found in co-pending U.S. Patent Application Ser. No. 61/468,614, which is incorporated herein by reference in its entirety and for all purposes. A particular illustrative embodiment is:

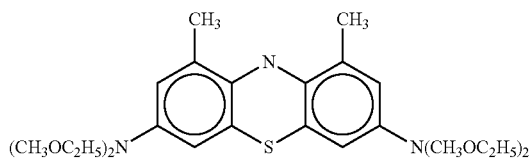

In still other embodiments of the invention, the method includes administering a compound having the structure of Compound 1 above wherein $R^3$ is oxo. Examples of such compounds are described in co-pending U.S. Patent Application Ser. No. 61/453,571, which is incorporated herein by reference in its entirety and for all purposes. In more particular embodiments, $R^3$ is oxo and each of $R^1$, $R^2$, $R^4$, $R^5$, $R^7$, and $R^8$ is hydrogen. In still more particular embodiments, $R^6$ is optionally substituted dialkylamino, and yet more particularly, $R^6$ is optionally substituted diethylamino or dimethylamino. In still more specific embodiments, $R^3$ is oxo and each of $R^1$, $R^2$, $R^4$, $R^5$, $R^7$, and $R^8$ is hydrogen, and $R^6$ is dimethylamino (Compound 6).

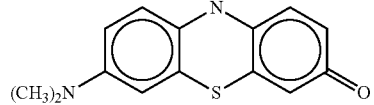

In still other embodiments, the method of the invention includes administering compounds having the structure shown in Compound 1 wherein each of $R^3$ and $R^6$ is optionally substituted four-, five-, six-, or seven-membered cycloheteroalkyl, the cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl. In more particular embodiments, each of $R^3$ and $R^6$ is optionally substituted five-membered cycloheteroalkyl, the cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl. Among the latter embodiments are those embodiments in which each of $R^3$ and $R^6$ is optionally substituted pyrrolidin-1-yl, and in still more particular embodiments, each of $R^3$ and $R^6$ is pyrrolidin-1-yl.

In more specific embodiments, the compound administered has the structure of Compound 1 wherein each of $R^3$ and $R^6$ is pyrrolidin-1-yl and each of $R^1$, $R^2$, $R^4$, $R^5$, $R^7$, and $R^8$ is hydrogen. In other embodiments, each of $R^3$ and $R^6$ is pyrrolidin-1-yl and each of $R^2$, $R^4$, $R^5$, and $R^7$ is hydrogen. Among these compounds, still more particular embodiments are those for which each of $R^1$ and $R^8$ is halo; and yet more particular embodiments are those for which each of $R^1$ and $R^8$ is chloro (Compound 7).

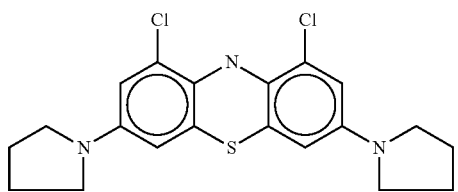

More examples of useful compounds having such structural features can be found in co-pending U.S. patent application Ser. No. 12/062,491, the entire disclosure of which is incorporated herein by reference in its entirety and for all purposes.

Returning to those embodiments of the method of the invention including administering compounds having the structure shown in Compound 1 wherein each of $R^3$ and $R^6$ is optionally substituted four-, five-, six-, or seven-membered cycloheteroalkyl, the cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl, still more particular embodiments among these include those embodiments for which each of $R^3$ and $R^6$ is optionally substituted four-membered cycloheteroalkyl, the cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl. Among these compounds are still more specific embodiments in which each of $R^3$ and $R^6$ is optionally substituted azetidin-1-yl. Yet more particular embodiments are those for which each of $R^3$ and $R^6$ is azetidin-1-yl.

Among the embodiments just described, i.e., the embodiments of Compound 1 for which each of $R^3$ and $R^6$ is azetidin-1-yl, particularly useful embodiment include those for which each of $R^1$, $R^2$, $R^4$, $R^5$, $R^7$, and $R^8$ is hydrogen (Compound 8).

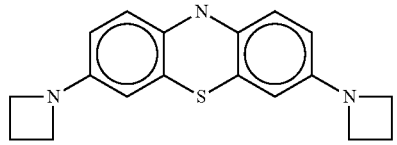

8

Among the embodiments just described, i.e., the embodiments of Compound 1 for which each of $R^3$ and $R^6$ is azetidin-1-yl, particularly useful embodiment include those for which each of $R^2$, $R^4$, $R^5$, and $R^7$ is hydrogen. Still more particular embodiments are those for which each of $R^2$, $R^4$, $R^5$, and $R^7$ is hydrogen and each of $R^1$ and $R^8$ is halo, and still more particularly, each of $R^1$ and $R^8$ is chloro (Compound 9).

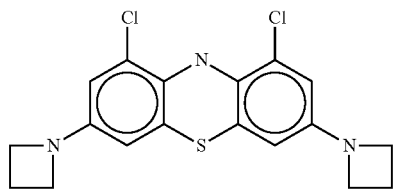

9

Still other embodiments include those variants of Compound 1, wherein one of $R^1$ and $R^8$ is hydrogen, and the other of $R^1$ and $R^8$ is selected from the group consisting of: hydrogen, halo, cyano, hydroxy, nitro, nitrilo, thio, amino, carboxyl, formyl, and optionally substituted alkyl. Among these compounds, more specific embodiments include those wherein one of $R^3$ and $R^6$ is optionally substituted dialkylamino, and the other of $R^3$ and $R^6$ is selected from the group consisting of: optionally substituted four-, five-, six-, or seven-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl. Of these, still more particular embodiments are those wherein at least one of $R^3$ and $R^6$ is optionally substituted diethylamino or dimethylamino, and still more particularly, wherein at least one of $R^3$ and $R^6$ is diethylamino or dimethylamino.

Among the embodiments just recited, more specific embodiments include those wherein one of $R^3$ and $R^6$ is five-, six-, or seven-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl; and more particularly those wherein one of $R^3$ and $R^6$ is six-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl.

In more specific embodiments including the compounds just recited, the optional second heteroatom is a second nitrogen heteroatom. Still more specific embodiments are those in which the six-membered ring is optionally substituted piperazin-1-yl. In still more specific embodiments having this general structure, $R^1$ is hydrogen, $R^3$ is optionally substituted piperazin-1-yl, $R^3$ is diethylamino or dimethylamino, $R^8$ is optionally substituted lower-alkyl, and each of $R^2$, $R^4$, $R^5$ and $R^7$ is hydrogen.

Yet more specific embodiments are those wherein $R^3$ is piperazin-1-yl, $R^3$ is diethylamino, and $R^8$ is optionally substituted ethyl or optionally substituted methyl. In one particular embodiment, $R^8$ is ethyl (Compound 10).

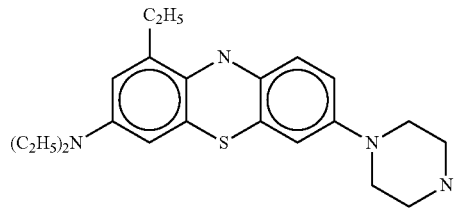

10

More examples of useful compounds having such structural features can be found in co-pending U.S. patent application Ser. No. 13/099,006, the entire disclosure of which is incorporated herein by reference in its entirety and for all purposes.

Other embodiments include those variants of Compound 1, wherein one of $R^1$ and $R^8$ is hydrogen, and the other of $R^1$ and $R^8$ is selected from the group consisting of: hydrogen, halo, cyano, hydroxy, nitro, nitrilo, thio, amino, carboxyl, formyl, and optionally substituted alkyl, and each of $R^3$ and $R^6$ is six-membered cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl. More specific embodiments from among these include those wherein said optional second heteroatom is an oxygen heteroatom, and, still more specifically, wherein said six-membered ring is optionally substituted morpholino. In yet more specific embodiments, the six-membered ring is morpholino. Still more specific embodiments are those further wherein $R^1$ is cyano, $R^8$ is hydrogen, and each of $R^2$, $R^4$, $R^5$ and $R^7$ is hydrogen (Compound 11).

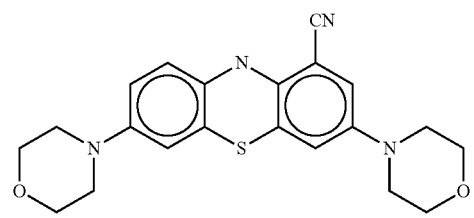

11

Still another useful 3-7-dimorpholino compound is:

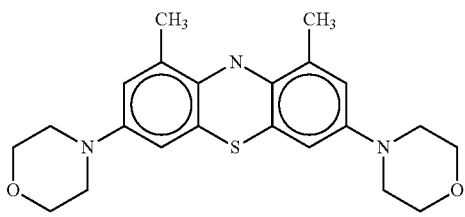

12

Still other useful embodiments of Compound 1, are those wherein one of $R^1$ and $R^8$ is hydrogen, and the other of $R^1$ and $R^8$ is selected from the group consisting of: hydrogen, halo, cyano, hydroxy, nitro, nitrilo, thio, amino, carboxyl, formyl, and optionally substituted alkyl, and one of $R^3$ and $R^6$ is six-membered cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl. More specific embodiments from among these include those wherein said optional second heteroatom is an oxygen heteroatom, and, still more specifically, wherein said six-membered ring is optionally substituted morpholino. In yet more specific embodiments, the six-membered ring is morpholino. In still more specific embodiments, the other of $R^3$ and $R^6$ is amino, substituted amino, or disubstituted amino. Exemplary substituted and disubstituted amino moieties include, but are not limited to, optionally substituted alkyl, including optionally substituted ethyl and optionally substituted methyl, and optionally substituted alkyloxyalkyl, including optionally substituted methyloxyethyl. Particular examples include the following:

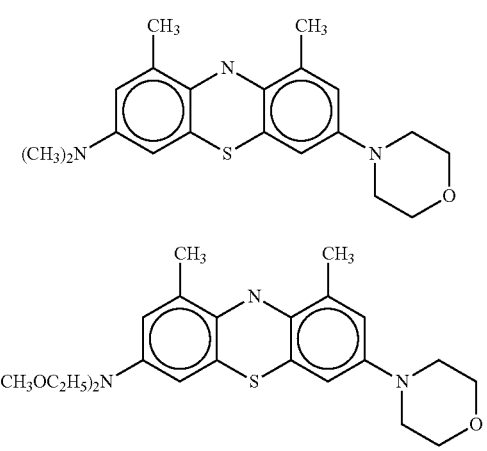

More examples of useful compounds having such structural features can be found in co-pending U.S. Patent Application Ser. No. 61/477,203, the entire disclosure of which is incorporated herein by reference in its entirety and for all purposes.

In a second aspect, the present invention provides a compound having the structure shown as Compound 1, but wherein $R^1$, $R^2$, $R^4$, $R^5$, $R^7$, and $R^8$ are selected independently from the group consisting of: hydrogen, halo, cyano, nitro, nitrilo, hydroxy, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cyclo alkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsulfonyl, cycloalkylsulfonyl, aralkycarbonylthioooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxyloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl; and at least one of $R^3$ and $R^6$ is optionally substituted azetidin-1-yl.

The compounds of the present invention can be used in the form of salts derived from inorganic or organic acids as will be familiar to those having ordinary skill in the art.

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, vaginal, and the like.

In accordance with other embodiments of the present invention, there is provided a composition comprising a compound described here, together with a pharmaceutically acceptable carrier or excipient. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Mack Pub. Co., New Jersey (1991), which is incorporated herein by reference.

Pharmaceutical compositions of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art.

While the compounds of the invention can be administered as the sole active pharmaceutical agent, they can also be used in combination with one or more other compound as described herein, or in combination with other agents used in the treatment or prevention of AD and related diseases, or both.

In addition, the compounds of the present invention can be used, either singly or in combination as described above, in combination with other modalities for preventing or treating AD and related diseases or disorders. Such other treatment modalities include without limitation, surgery, radiation, hormone supplementation, and diet regulation. These can be performed sequentially (e.g., treatment with a compound of the invention following surgery or radiation) or in combination (e.g., in addition to a diet regimen).

The additional active agents may generally be employed in therapeutic amounts as indicated by sources well known to those having ordinary skill in the art, e.g., the PHYSICIAN'S DESK REFERENCE (PDR) 53$^{rd}$ Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

In accordance with yet other embodiments, the present invention provides methods for treating or preventing AD or similar disorder in a human or animal subject in which an amount of a compound of the invention that is effective to at least ameliorate disease symptoms. Effective amounts of the compounds of the invention generally include any amount sufficient to detectably modulate AD using standard measures, by other methods known to those having ordinary skill in the art, or by detecting prevention or alleviation of symptoms in a subject afflicted with AD.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes of the present invention, a prophylactically or therapeutically effective dose will generally be from about 0.1 mg kg$^{-1}$ d$^{-1}$ to about 100 mg kg$^{-1}$ d$^{-1}$, preferably from about 1 mg kg$^{-1}$ d$^{-1}$ to about 20 mg kg$^{-1}$ d$^{-1}$, and most preferably from about 10 mg kg$^{-1}$ d$^{-1}$ to about 10 mg

3.3 EXAMPLES

3.3.1 Synthesis of Compounds

The compounds of the present invention can be synthesized using techniques and materials known to those of skill in the art. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy ("IR" and "UV"), X-ray crystallography, elemental analysis ("EA"). HPLC and mass spectroscopy ("MS") can be used for identification, quantitation and purification as well.

Although the schemes below illustrate specific starting materials and products, those having ordinary skill in the art will understand that many substitution patterns can be made using known methods and materials in combination with the teachings herein.

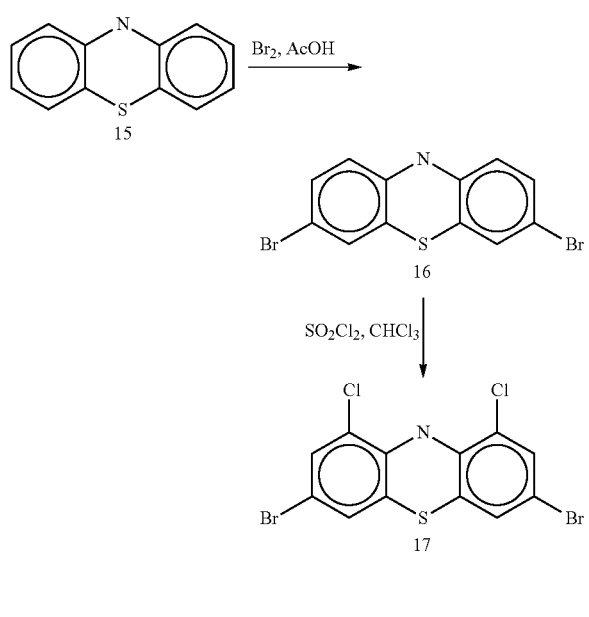

3,7-Dibromo-10H-phenothiazine (16)

5.0 g (25 mmol) of phenothiazine (15) was suspended in 200 mL of glacial AcOH. Then, 3.3 mL Br$_2$ (0.63 mol) in 200 mL of glacial was slowly added to the reaction mixture and stirred for 16 h at room temperature. The reaction was cooled with an ice bath and 6.30 g (50 mmol) of Na$_2$SO$_3$ was added to the reaction mixture. By adding a little water (3.0 mL), a deep-violet color formed within three hours. After the addition of a solution of 4.10 g (62 mmol) of KOH dissolved in water (1.0 L) a greenish solid forms which was washed with a little cold 2-propanol. The solid was recrystallized with 2-propanol to give 7.90 g (88%) as a green powder.

3,7-Dibromo-1,9-dichloro-10H-phenothiazine (17)

The 3,7-dibromophenothiazine (6.25 g, 17.5 mmol) was dissolved in 200 mL of chloroform (CHCl$_3$). Sulfuryl chloride (SO$_2$Cl$_2$, 3.13 mL, 38.5 mmol) was added dropwise over 15 min. The dark mixture was stirred at RT for 36 h. The mixture was then filtered and the solid washed with CHCl$_3$. The solid was collected and stirred in Et$_2$O and the resulting green solid was filtered off and dried under vacuum to give a quantitative yield of the desired product.

tert-Butyl 3,7-dibromo-1,9-dichloro-10H-phenothiazine-10-carboxylate

The 3,7-dibromo-1,9-dichloro-10H-phenothiazine (10.00 g, 23.47 mmol) was suspended in CH$_3$CN (200 mL) and dimethylaminopropylamine (DMAP, 2.87 g, 23.47 mmol) was added. The mixture was heated at reflux (near 85° C.) and Boc$_2$O (15.16 g, 70.41 mmol) dissolved in CH$_3$CN (50 mL) was added dropwise over 1 h. The reaction mixture became homogeneous and turned brown. The reaction was allowed to cool to RT and the solvent was evaporated. The residue was purified by flash silica gel chromatography to give a 95% yield.

3,7-di(azetidin-1-yl)-1,9-dichlorophenothiazin-5-ium 2,2,2-trifluoroacetate (9)

The tert-Butyl 3,7-dibromo-1,9-dichloro-10H-phenothiazine-10-carboxylate (250 mg, 0.473 mmol) was combined with Pd$_2$dba$_3$ (20 mg, 0.033 mmol), BINAP (80 mg, 0.031 mmol), Cs$_2$CO$_3$ (380 mg, 1.19 mmol), azetidine hydrochloride (97.0 mg, 1.04 mmol), and xylenes (10 mL). The resulting mixture was heated at reflux for 24 h. The reaction was allowed to cool to RT and the solvent was evaporated to give a residue. The residue was extracted with ethyl acetate (EtOAc) and brine. The organic layer was dried over MgSO$_4$, filtered and evaporated to give a residue. The residue was dissolved in CH$_2$Cl$_2$ (5 mL) and trifluoroacetic acid (TFA) (5 mL) and stirred overnight at RT. The solvent was evaporated and the residue purified by flash silica gel chromatography to give 28 mg of the desired product for a 12% yield over the two steps. LC/MS confirmed correct product.

1-cyanophenothiazine

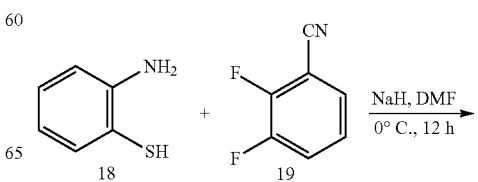

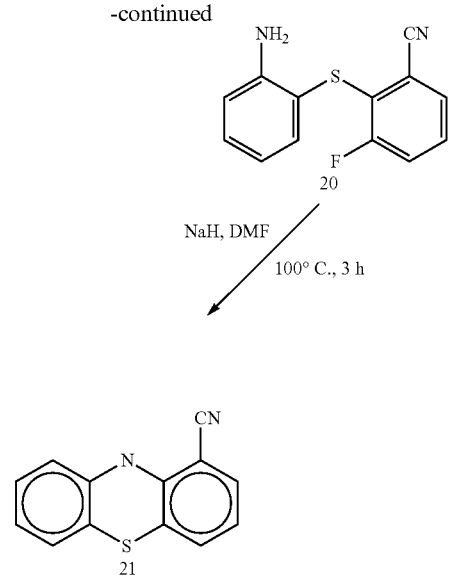

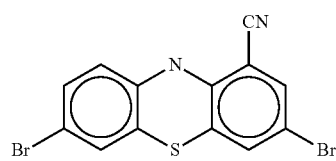

Prepared 1-cyanophenothiazine (21) via 20 as described in the literature (Neale, R. H. and Driscoll, J. S. "1-Substituted phenothiazine derivatives (II)", *Journal of Heterocyclic Chemistry* (1967), vol. 4, pp. 587-590) starting from 2-aminobenzenethiol (18, 2.1 mL, 2.46 g, 20 mmol), 2,3-difluorobenzonitrile (19, 1.9 mL, 2.83 g, 20 mmol), and sodium hydride (1.09 g, 27.3 mmol) in 10 mL, of dimethyl fumarate (DMF). After crystallizing from dichloromethane-ethanol, obtained 1-cyanophenothiazine as a dark yellow powder (1.342 g, 6 mmol, 30% yield).

3,7-dibromo-10H-phenothiazine-1-carbonitrile

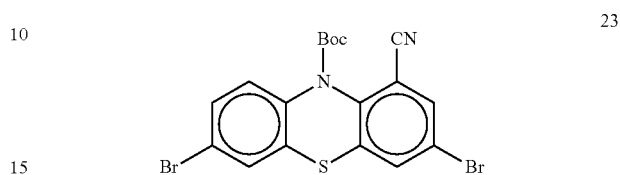

Bromination performed as described in the literature (Bromo and thiocyanato derivatives of 10-methylphenothiazine. Bodea, C. and Terdic, M. *Acad. Rep. Populare Romine, Filiala Cluj, Studii Cercetari Chim.* (1962), 13(1), 81-7) starting from 1-cyanophenothiazine (21, 290 mg, 1.29 mmol) instead of phenothiazine, acetic acid (9.3 mL), and bromine (0.165 mL, 3.21 mmoles, 2.5 eq.) in acetic acid (1 mL). Performed workup as described in the literature using sodium sulfite (343 mg, 2.72 mmol, 2 eq.) then after 15 min, deionized water (1 mL).

Put potassium hydroxide (200 mg, 3.56 mmol, 2.75 eq.) in 15 mL of deionized water and brought the volume up to 40 mL with ice. Added the above reaction mixture to get a dark brown precipitate and stirred for 2 h to overnight. Filter off the precipitate, rinse with more deionized water, then placed under vacuum overnight to obtain the desired product (22) as a brown flakes without further purification (354.9 mg, 0.929 mmol, 72% yield).

tert-butyl 3,7-dibromo-1-cyano-10H-phenothiazine-10-carboxylate (23)

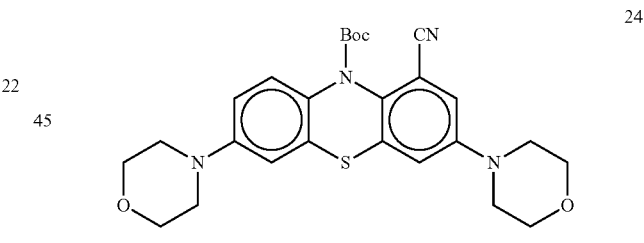

Performed the Boc anhydride protection of 3,7-dibromo-10H-phenothiazine-1-carbonitrile (22) as described in the literature. Alternatively, to a vial containing the aforementioned dibromocyanophenothiazine (300 mg, 0.785 mmol) was added crushed DMAP (61 mg, 0.499 mmol) followed by acetonitrile (3 mL). The suspension was heated to 85° C. then crushed Boc$_2$O was added (about 346 mg, 1.57 mmol, 2 eq.) dissolved in acetonitrile (2 mL). Refluxed under argon overnight.

Removed solvent under vacuum when complete (checked by LC/MS and TLC), dissolved in dichloromethane, extracted with deionized water once then diluted 2N phosphoric acid (pH=2) once, then with deionized water again until neutral (2×). Dried organic layers over sodium sulfate then remove solvent under vacuum. Dissolved in acetone then add isopropanol until precipitate appeared. Alternatively, purified using Isco column chromatography (5% methanol/95% dichloromethane). Obtained product (23) as a crimson residue (355.3 mg, 0.737 mmol, 94% yield).

tert-butyl 1-cyano-3,7-dimorpholino-10H-phenothiazine-10-carboxylate (24)

Performed the reaction as described in the literature with (Toshihiro Okamoto, et al. "Remarkable structure deformation in phenothiazine trimer radical cation", *Organic Letters*, (2004), vol. 6, #20, pp. 3493-3496) the following variances in starting materials and catalysts.

Suspended tert-butyl 3,7-dibromo-1-cyano-10H-phenothiazineL-10-carboxylate (355.3 mg, 0.737 mmol) in m-xylene (4 mL). Added morpholine (0.065 mL, 0.739 mmol), Pd(dba)$_2$ (19 mg, 0.033 mmol), cesium carbonate (1.2 g, 3.68 mmol), then BINAP (25 mg, 0.040 mmol). Stir at 90° C.-90° C. for 2 h under argone. Removed solvent under vacuum and use the monoamine in the next step without further purification.

Add the same amount of catalysts and solvents with the exception of morpholine (0.095 mL, 1.08 mmol). Stir at 120°-130° C. overnight. Filtered off solids then removed solvent under vacuum. Purified using Isco column chromatography (5% methanol/95% dichloromethane). Obtained product 24 as dark yellow-brown residue (83 mg, 0.168 mmol, 23% yield).

2,2,2-trifluoroacetic acid,
1-cyano-3,7-dimorpholinophenothiazin-5-ium salt

Dissolved tert-butyl 1-cyano-3,7-dimorpholino-10H-phenothiazine-10-carboxylate (63.0 mg, 0.0.127 mmol) in dichloromethane (3 mL). Added TFA (2 mL, 27 mmol). Stirred until the reaction was complete by TLC and LC/MS (2 h).

Removed solvent under vacuum. Purified on a silica column using a dichloromethane-methanol gradient. Obtained product (64 mg, 0.127 mmol, quantitative yield).

1-Ethyl-10H-phenothiazine (25)

To a solution of 10H-phenothiazine (15, 3.75 g, 18.8 mmol) in THF (100 mL) cooled to −78° C. was added a solution of n-butyl lithium (n-BuLi) (9.1 mL, 22.78 mmol, 2.5 M in hexanes) The mixture was stirred for 1 h at −78° C. and allowed to warm to room temperature. The mixture was again cooled to −78° C. and $CO_2$ (g) was bubbled directly into the solution for 5 min. The mixture was stirred at −78° C. for 1 h, and then allowed to warm to RT overnight.

The solution was evaporated to dryness and re-dissolved in THF (100 mL) and cooled to −78° C. To this solution was added tert-butyl lithium (t-BuLi) (t8.7 mL, 28.05 mmol, 1.5 M in pentane) dropwise. The mixture was stirred at −78° C. for 1 hour then allowed to warm to −23° C. and stirred at this

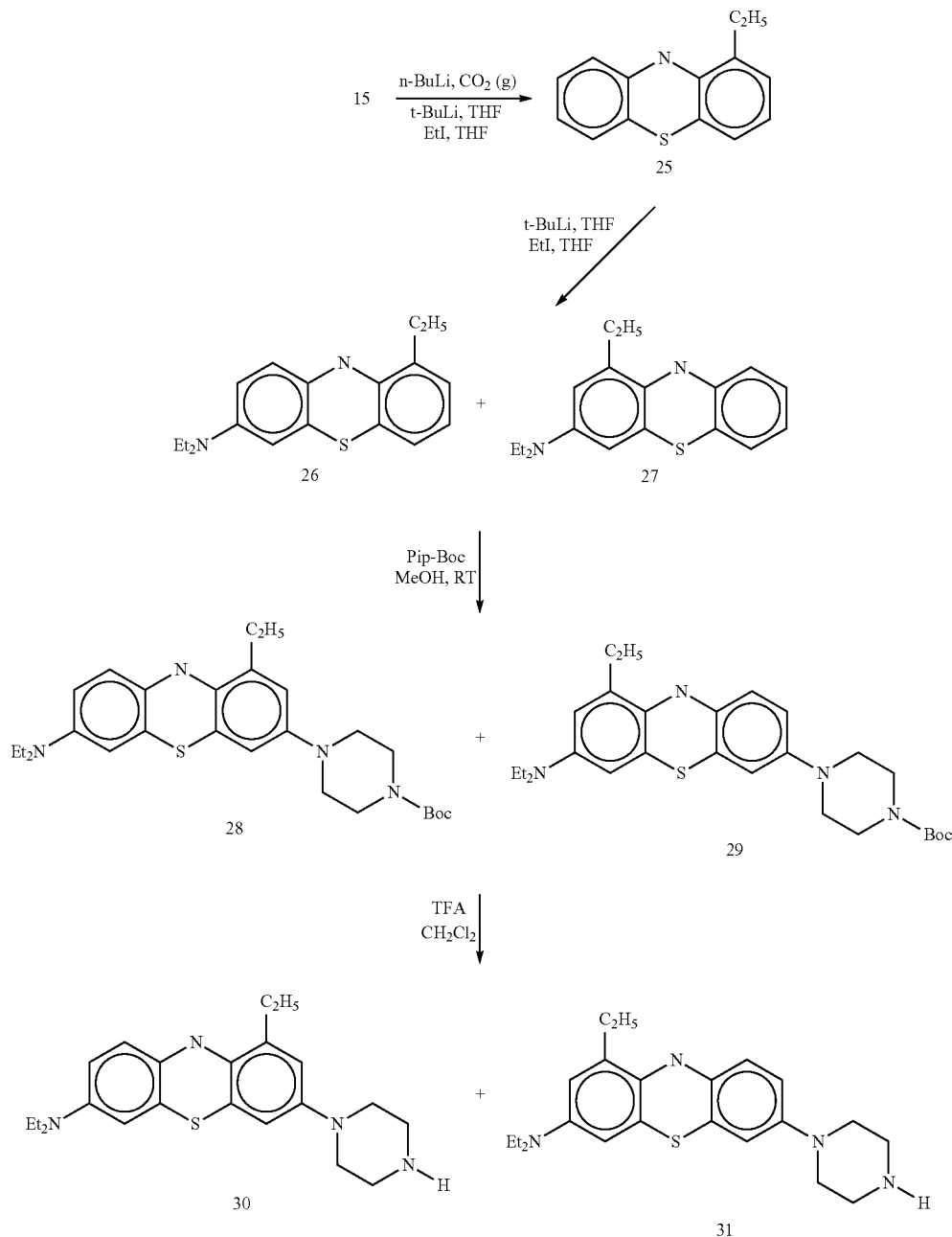

temperature for 4 h. The mixture was cooled to −78° C. and ethyl iodide (2.5 mL, 37.6 mmol) was added dropwise. The resulting mixture was stirred for 1 h at −78° C. and then allowed to warm to RT overnight.

The reaction mixture was quenched with ice cold 1 M $H_3PO_4$ and extracted three times with EtOAc. The combined organic layeres were washed with brine, dried over $MgSO_4$, filtered and evaporated to give a residue. The residue was purified by flash silica gel chromatography to give 3.2 g of a tan solid for a 75% yield. LC/MS was correct for the product (25).

1-Ethyl-phenothiazin-5-ium iodide

1-Ethyl-10H-phenothiazine (646 mg, 2.84 mmol) was dissolved in $CHCl_3$ (10 mL) and cooled to 0° C. as a solution of Iodine (2.16 g, 8.51 mmol) dissolved in $CHCl_3$ (50 mL) was added dropwise. The mixture was stirred at 0° C. for 2 h, then allowed to warm to RT overnight.

The solvent was evaporated from the mixture and pentane (50 mL) was added. The mixture was stirred for 1 h at RT and filtered to give a dark solid. The solid was dried under vacuum overnight.

3-(diethylamino)-1-ethylphenothiazin-5-ium iodide (and 7-(diethylamino)-1-ethylphenothiazin-5-ium iodide) (26 and 27)

The phenothiazine salt (500 mg, 0.681 mmol) was combined with $CHCl_3$ (10 mL) and $Et_2NH$ (0.15 mL, 1.5 mmol) and stirred at RT overnight. The solvent was evaporated from the mixture, and the residue was stirred in pentane. The resulting dark powder was filtered off and used without further purification.

7-(4-(tert-butoxycarbonyl)piperazin-1-yl)-3-(diethylamino)-1-ethylphenothiazin-5-ium and 3-(4-(tert-butoxycarbonyl)piperazin-1-yl)-7-(diethylamino)-1-ethylphenothiazin-5-ium (28 and 29)

The crude product mixture of 3-(diethylamino)-1-ethylphenothiazin-5-ium iodide and 7-(diethylamino)-1-ethylphenothiazin-5-ium iodide was added to a solution of N-Boc-piperazine (177 mg, 0.95 mmol, "Pip-Boc") and MeOH (10 mL) the resulting mixture was stirred at RT for 24 h. The solvent was evaporated to dryness and used without purification in the next step.

2,2,2-trifluoroacetic acid, 3-(diethylamino)-1-ethyl-7-(piperazin-1-yl)phenothiazin-5-ium salt and 2,2,2-trifluoroacetic acid, 7-(diethylamino)-1-ethyl-3-(piperazin-1-yl)phenothiazin-5-ium salt (30 and 31)

The crude mixture of 7-(4-(tert-butoxycarbonyl)piperazin-1-yl)-3-(diethylamino)-1-ethylphenothiazin-5-ium and 3-(4-(tert-butoxycarbonyl)piperazin-1-yl)-7-(diethylamino)-1-ethylphenothiazin-5-ium was dissolved in $CH_2Cl_2$ (5 mL) and TFA (5 mL) and heated at 70° C. for 2 h. The reaction was followed by TLC. When all of the starting material was consumed, the reaction was allowed to cool to room temperature and the solvent was evaporated to give a residue. The residue was purified with Prep Plate TLC to give two regioisomer products. The more polar product isolated was 2,2,2-trifluoroacetic acid, 7-(diethylamino)-1-ethyl-3-(piperazin-1-yl) phenothiazin-5-ium(30) in 6.3 mg; the less polar product was 2,2,2-trifluoroacetic acid, 3-(diethylamino)-1-ethyl-7-(piperazin-1-yl)phenothiazin-5-ium (31) with 18 mg isolated.

3.4 Testing and Biological Activity of Compounds

Compounds of the invention, including those described above, were tested in an activity assay prepared and used as follows.

3.4.1 Assay for Activity Against Aβ

Day 1: Seeded $3 \times 10^5$ 7 Pa2 cells/10 cm dish in 7.5 mL Dulbecco's Modified Eagle's Medium (DMEM). Correspondingly, wild-type CHO cells were prepared as a control. The cells were exposed to compounds.

Day 5: The cell medium was changed to Dulbecco's Modified Eagle's Medium-Fetal Calf Serum (DMEM-FCS) (7.5 mL). The cells were again exposed to test compounds.

Day 8: The supernatants from the cell cultures were harvested in a 15 mL falcon tube. The cell debris was spun down (5 min at 4,000 G, and the supernatant was transferred to a fresh 15 mL falcon tube, and 100 µL of IC16-NHS-Sepharose-slurry (20 µL) was added. The solution was incubated over night at 4° C. using an end-over-end shaker. The cells were then washed with phosphate-buffered saline (PBS) and scraped and placed in 1 mL of a buffer (TBS, 5 mmol EDTA, 1% Triton, and protease inhibitors. The lysates were then frozen (−20° C.).

Day 9: The beads were spun down (5 min at 4,000 G) and transferred to 1.5 mL eppi tubes each holding 1 mL PBS and spun down again (1 min at 5,000 rpm. The step of spinning, transferring, and spinning was repeated. The remaining PBS was removed and 25 µL of Tris/Tricine loading buffer, without reducing agent, was added, and the mixture was boiled for 5 min at 95° C. The sample was separated on a 10%-20% Tris/Tricine Peptide gel (biorad) using a 1× Tris/Tricine running buffer for approximately 2.5 h at 120 V. A power blot on 0.2 µm NC-membrane was done with fresh transfer buffer over 2 h at 400 mA; the blot was boiled in a microwave 7 min in a 1:1 PBS:water mixture. The membrane was blocked in PBST/milk over night at 4° C.

Day 10: The blocking solution was collected for secondary antibody incubation. The blot was washed with pure water and incubated with 4G8 (1:200 in PBST, $NaN_3$) in a foil bad with at least 7 mL antibody solution and shaken for 3 h at room temperature on a shaker. The antibody solution was collected, a blot washed three times with PBST, and incubated with secondary antibody (1:25000 in blocking solution, goat-anti-mouse-POD). The blot was then washed three times with PBST and developed with ECL with exposure times of 1 min, 5 min, 15 min, 60 min, and over night.

3.4.2 Compounds Having Activity Against Aβ

Out of a set of approximately 50 compounds, approximately ten, those particular compounds illustrated herein, showed some degree of Aβ oligomer formation diminution. Two of the compounds (10 and 11) were extremely robust, with no significant effect on protein synthesis, displaying $EC_{50}$ values of approximately 40 nM and demonstrating potent anti-Aβ oligomer forming activity and thus are potential therapeutics for AD. Not wishing to be held to any particular theory of action or activity, of particular interest is the implication from these results that compounds of the invention target host multiprotein complexes that are molecular "machines that build machines". This hypothesis is further supported by similarities between the compounds of the invention and broad-spectrum antiviral compounds described in PCT Publication WO 2008/124550, which is incorporated herein by reference in its entirety and for all purposes.

Compounds described herein also showed effectiveness at disrupting Aβ formation as demonstrated. Hennes 20 cells that stably express Aβ oligomers were treated with test compounds in a dose titration as described herein, and the distribution of Aβ peptide among trimers, dimers and monomers was determined as described herein. $EC_{50}$ values were determined for the conversion of trimer+dimer to monomer, and for the disappearance of oligomers (dimers and trimers).

Robust activity was observed by both assays for several chemical series. Compound 5 showed $EC_{50}$ values of 0.032 μM and 0.041 μM for Aβ trimer-to-monomer formation and prevention of oligomerization, respectively. Compound 6 showed $EC_{50}$ values of 0.338 μM and 0.856 μM for Aβ trimer-to-monomer formation and prevention of oligomerization, respectively. Compound 7 was found to have $EC_{50}$ values of 0.005 μM and 0.023 μM for Aβ trimer-to-monomer formation and prevention of oligomerization, respectively. Compound 8 was found to have $EC_{50}$ values of 0.047 μM and 0.176 μM for Aβ trimer-to-monomer formation and prevention of oligomerization, respectively. Compound 10 was found to have $EC_{50}$ values of 0.019 μM and 0.904 μM for Aβ trimer-to-monomer formation and prevention of oligomerization, respectively. Compound 11 was found to have $EC_{50}$ values of 0.047 μM and 0.176 μM for Aβ trimer-to-monomer formation and prevention of oligomerization, respectively. Compound 12 was found to have $EC_{50}$ values of 0.017 μM and 0.03 μM for Aβ trimer-to-monomer formation and prevention of oligomerization, respectively. Compound 13 was found to have $EC_{50}$ values of 0.017 μM and 0.064 μM for Aβ trimer-to-monomer formation and prevention of oligomerization, respectively. Compound 14 was found to have $EC_{50}$ values of 0.164 μM and 0.168 μM for Aβ trimer-to-monomer formation and prevention of oligomerization, respectively.

In addition, Compound 10 was found to bind the proteins CutA and peroxire-doxin 6, both of which have been implicated in the etiology of Alzheimer's Disease.

4. CONCLUSION

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

What is claimed:

1. A method for treating Alzheimer's Disease, comprising administering to a mammal suffering from such disease a therapeutically effective amount of a compound having the structure:

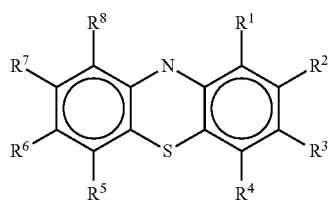

and its pharmaceutically acceptable salts, and hydrates, wherein:
$R^1$ is halo or optionally substituted alkyl,
$R^2$, $R^4$, $R^5$, $R^7$, and $R^8$ are selected independently from the group consisting of: hydrogen, halo, cyano, nitro, nitrilo, hydroxy, thio, amino, carboxyl, formyl, and optionally substituted alkyl, alkylcarbonyloxy, arylcarbonyloxy, heteroarylcarbonyloxy, cycloalkylcarbonyloxy, cyclo-heteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsulfonyl, cycloalkylsulfonyl, aralkycarbonylthioooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl;

$R^3$ and $R^6$ are selected independently from the group consisting of: optionally substituted four-, five-, six-, or seven-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl; and oxo, thiocarbonyl, imino, and optionally substituted dialkylimino, diarylimino, diheteroarylimino, alkylarylimino, alkylheteroarylimino, arylheteroarylimino, amino, alkylamino, dialkylamino, alkyloxyalkylamino, di-(alkyloxyalkyl)amino, alkylthioalkylamino, di-(alkylthioalkyl)amino, alkylaminoalkylamino, di-(alkylaminoalkyl)amino, aryloxyalkylamino, di(aryloxyalkyl)amino, arylthioalkylamino, di-(arylthioalkyl)amino, arylaminoalkylamino, di-(arylaminoalkyl)amino, heteroaryloxyalkylamino, di-(heteroaryloxyalkyl)amino, heteroarylthioalkylamino, di-(heteroarylthioalkyl)amino, heteroarylaminoalkylamino, and di-(heteroarylaminoalkyl)amino; and at least one of $R^3$ and $R^6$ is optionally substituted five-, six-, or seven-membered cycloheteroalkyl, said cycloheteroalkyl including a first ring nitrogen heteroatom bonded at the position indicated by $R^3$ or $R^6$, respectively.

2. The method of claim 1, wherein $R^3$ is oxo.

3. The method of claim 1, wherein each of $R^3$ and $R^6$ is optionally substituted four-, five-, six-, or seven-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl.

4. The method of claim 3, wherein each of $R^3$ and $R^6$ is optionally substituted five-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl.

5. The method of claim 4, wherein each of $R^3$ and $R^6$ is optionally substituted pyrrolidin-1-yl.

6. The method of claim 5, wherein each of $R^3$ and $R^6$ is pyrrolidin-1-yl.

7. The method of claim 6, wherein each of $R^2$, $R^4$, $R^5$, $R^7$, and $R^8$ is hydrogen.

8. The method of claim 3, wherein each of $R^3$ and $R^6$ is optionally substituted four-membered cycloheteroalkyl, said cycloheteroalkyl including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl.

9. The method of claim 8, wherein each of $R^3$ and $R^6$ is optionally substituted azetidin-1-yl.

10. The method of claim 9, wherein each of $R^3$ and $R^6$ is azetidin-1-yl.

11. The method of claim 10, wherein each of $R^2$, $R^4$, $R^5$, $R^7$, and $R^8$ is hydrogen.

12. The method of claim 1, wherein $R^8$ is hydrogen, and each of $R^3$ and $R^6$ is a six-membered cycloheteroalkyl ring including a first ring nitrogen heteroatom bonded at the position indicated by $R^3$ and $R^6$, respectively, and an optional second heteroatom selected from the group consisting of optionally substituted nitrogen, oxygen, sulfur, sulfinyl, and sulfonyl.

13. The method of claim 12, wherein said optional second heteroatom is an oxygen heteroatom.

14. The method of claim 12, wherein said six-membered cycloheteroalkyl ring is morpholino.

15. The method of claim 1, wherein said compound is

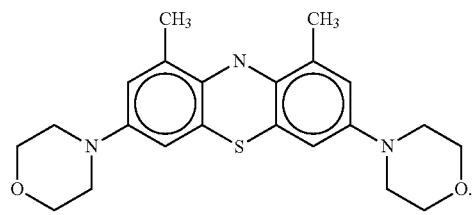

16. The method of claim 1, wherein $R^8$ is hydrogen, and one of $R^3$ and $R^6$ is a six-membered cycloheteroalkyl ring including a first ring nitrogen heteroatom bonded at the position indicated by $R^3$ or $R^6$, respectively, and an optional second heteroatom selected from the group consisting of optionally substituted nitrogen, oxygen, sulfur, sulfinyl, and sulfonyl.

17. The method of claim 16, wherein said optional second heteroatom is an oxygen heteroatom.

18. The method of claim 16, wherein said six-membered cycloheteroalkyl ring is morpholino.

19. The method of claim 1, wherein at least one of $R^3$ and $R^6$ is optionally substituted azetidin-1-yl.

* * * * *